United States Patent

Krause et al.

[11] Patent Number: 5,589,398
[45] Date of Patent: Dec. 31, 1996

[54] USE OF TEST STRIPS TO DETERMINE THE UV INTENSITY OR TO PRE-DETERMINE THE DURATION OF STAY IN THE SUN WITHOUT SUNBURN

[75] Inventors: Manfred Krause, Viernheim; Norbert Kaufmann, Ruppertsberg; Mathias Neumann, Weinheim, all of Germany

[73] Assignee: Boehringer Mannheim GmbH, Mannheim, Germany

[21] Appl. No.: 340,394

[22] Filed: Nov. 15, 1994

[30] Foreign Application Priority Data

Nov. 15, 1993 [DE] Germany ............... 43 38 811.6

[51] Int. Cl.⁶ .................. G01N 31/22; G01N 21/17
[52] U.S. Cl. ................. 436/164; 436/166; 422/58; 422/61
[58] Field of Search ................... 422/56, 58, 61; 436/166, 164

[56] References Cited

U.S. PATENT DOCUMENTS

| | | | |
|---|---|---|---|
| 3,903,423 | 9/1975 | Zweig | 250/474 |
| 4,065,672 | 12/1977 | Harpster | 250/372 |
| 4,130,766 | 12/1978 | Fanselow et al. | 250/474 |
| 4,372,680 | 2/1983 | Adams et al. | 356/51 |
| 4,818,491 | 4/1989 | Fariss | 422/56 |
| 4,882,598 | 11/1989 | Wulf | 250/338.1 |
| 4,962,910 | 10/1990 | Shimizu | 250/372 |
| 5,008,548 | 4/1991 | Gat | 250/372 |
| 5,028,792 | 7/1991 | Mullis | 250/474.1 |
| 5,075,557 | 12/1991 | Harasawa et al. | 250/474.1 |
| 5,240,860 | 8/1993 | Hoenes et al. | 436/111 |
| 5,382,523 | 1/1995 | Hoenes et al. | 435/14 |

FOREIGN PATENT DOCUMENTS

| | | |
|---|---|---|
| 78753/81 | 7/1982 | Australia . |
| 11207/83 | 8/1983 | Australia . |
| 65985/86 | 6/1987 | Australia . |
| 10200/88 | 7/1988 | Australia . |
| 29176/89 | 8/1989 | Australia . |
| 30967/89 | 9/1989 | Australia . |
| 0431456A1 | 11/1990 | European Pat. Off. . |
| 0562201A1 | 9/1993 | European Pat. Off. . |
| 89/12218 | 12/1989 | WIPO . |
| 92/12403 | 7/1992 | WIPO . |
| 93/18377 | 9/1993 | WIPO . |

*Primary Examiner*—Lyle A. Alexander
*Attorney, Agent, or Firm*—Nikaido Marmelstein Murray & Oram LLP

[57] ABSTRACT

The invention concerns the use of test strips with a flat, preferably oblong foil which carries a matrix containing a photoactive chromogenic substance to pre-determine the duration of stay in the sun that is possible without sunburn, a test system for this determination containing test strips and a test strip pack, a test strip pack and a method for the pre-determination of the maximum possible duration of stay in the sun without sunburn using the test system.

7 Claims, 4 Drawing Sheets

| 0 | 1 | 2 | 3 | 4 | 5 | SKIN TYPE |
|---|---|---|---|---|---|---|
| 1h 50min. | 45min. | 20min. | 10min. | 5min. | | I |
| 2h 20min. | 1h | 30min. | 15min. | 7min. | | II |
| 3h | 1h 20min. | 40min. | 20min. | 10min. | | III |
| 4h | 1h 45min. | 50min. | 25min. | 12min. | | IV |

USE OF TEST STRIPS TO DETERMINE THE UV INTENSITY OR TO PRE-DETERMINE THE DURATION OF STAY IN THE SUN WITHOUT SUNBURN

The invention concerns the use of test strips to determine the UV intensity or to pre-determine the duration of stay in the sun without sunburn. In addition the invention concerns a suitable corresponding test system with test strips and a test strip pack. The invention also concerns a method to pre-determine the maximum possible duration of stay in the sun without sunburn.

Intensive short-wave ultraviolet radiation such as that which is pan of sunlight can lead not only to light erythema, sunburn and skin necroses but under certain circumstances also to skin cancer if the duration of exposure to the damaging radiation is long enough. It is believed that an increased incidence of skin cancer can be associated with the ozone reduction of the troposphere. Persons who have to expose themselves to sunlight such as for example persons who work outdoors therefore have in this regard an increased health risk. On the other hand skin tanning by sunlight is widely regarded as a characteristic of health. This applies particularly to pale skinned inhabitants of the earth who attempt to tan their skin by sunbathing.

Since wide sections of the population have become aware of the hazardous effects of sunlight to health, solutions are sought which correlate the current UV intensity with advice about the period of exposure to the sun after which a person has to expect sunburn.

There are relatively expensive instruments for this which are for example worn on the wrist like a watch which make an integral measurement of the current UV intensity and give a warning signal when the allowed period has been exceeded. Apart from the high price, such instruments have the disadvantage that when the wearer is in an upright posture considerably lower values are measured on the wrist due to the non-perpendicular incidence of the radiation than when the wearer is in a lying position with the instrument directed towards the sun or on exposed skin surfaces such as the nose or shoulders.

Photoactive substances which, depending on the UV intensity and exposure time, reversibly or irreversibly change their colours are known. A disadvantage of reversible substances in this connection is that they lose their reactibility after certain periods of exposure and therefore no longer revert to their original colour state. The test must therefore always be stored protected from light. In addition the formation of colour by such substances is dependent on temperature which, at constant UV intensity, leads to very large differences in the results, if for example measurements are carried out with the same substance in high mountains or on the beach.

Substances which irreversibly change their colour on UV exposure are known in the form of labels which are to be adhered to the skin. A disadvantage of these specific embodiments is that pale patches remain at the adhesion sites after sunbathing. Moreover the user of such tests does not know in advance how long he may expose himself to the sun but only when he has reached the limit. A pre-planning is not possible with this test. If the adhesive labels which carry the photoactive substance are stuck on body sites which are exposed to sunlight such as the face, nose or shoulders, then it is impossible or at best extremely difficult for the wearer himself to read these labels without removing them from that part of the body. However, each time the label is removed the adhesive strength decreases so that either the label can no longer be attached as intended or, if for this reason one wishes to avoid detaching the label, it is not possible to rule out the risk that one fails to notice the time at which it warns against a sunburn.

The object of the present invention was therefore to provide a means with which the UV intensity can be determined simply and cheaply and which can be used to pre-determine the maximum possible duration of stay in the sun without sunburn.

This object is achieved by the subject matter of the invention as characterized in the claims.

The invention concerns the use of test strips each with a flat, preferably oblong foil which carries a matrix containing a photoactive chromogenic substance for the determination of the UV intensity of light and in particular to pre-determine the possible duration of stay in the sun that is possible without sunburn.

The invention also concerns a test system for the determination of UV intensity containing test strips which are each essentially composed of a flat, preferably oblong foil carrying a matrix containing a photoactive, chromogenic substance wherein the test strips are protected if desired from light and are individually packaged and a test strip pack which is suitable for holding test strips that are each essentially composed of a flat, preferably oblong foil carrying a matrix containing a photoactive, chromogenic substance. The test strip pack according to the invention is essentially composed of a container which is suitable for holding the test strips and of a device which enables the test strip pack to be hung up on a pin. The pack is characterized in that the container is a box which essentially has the form of a cuboid with edges a, b and c and with six flat boundary surfaces in which the edges a, b and c can all be of the same length or of different lengths or two can be of the same length and one can be of a different length to this. Correspondingly the six flat boundary, surfaces can also all be the same such as in a cube or can be different in pairs such as in a compressed cube (two of the edges a, b and c are the same) or in a cuboid which is bounded only by rectangular and not quadrangular surfaces (the edges a, b and c are all different). One of the flat surfaces bounding the cuboid extends the cuboid and carries the hanging device. In addition the regular edge of the cuboid nearest to the hanging device is replaced completely or partially by two edges which are essentially parallel to one another and to the regular edge of the cuboid. The hanging device and one or both parallel edges are in such a geometric relation to one another that a straight line from one or both parallel edges aimed through the hanging device forms a certain angle with the flat surface protruding beyond the limits of the cuboid.

The invention in addition concerns a test strip pack as described above as part of the test system according to the invention.

Furthermore the invention concerns a method to pre-determine the maximum possible duration of stay in the sun without sunburn using a test system as described above which is characterized in that a test strip composed of a flat, preferably oblong foil carrying a matrix containing a photoactive chromogenic substance is exposed for a certain period to sunlight and is subsequently compared with a reference scale with different colour zones whereupon the maximum possible duration of stay in the sun without sunburn can be read from the colour zone of the reference scale which is closest to the colour of the matrix containing the photoactive chromogenic substance.

In the following the invention is elucidated in more detail on the basis of drawings illustrating a possible embodiment.

Figure 1A:
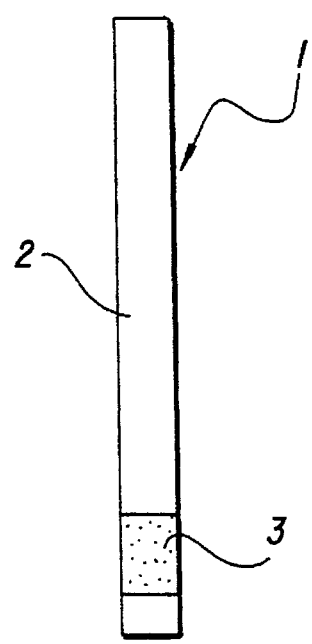
FIG. 1a) shows a test strip for the determination of the UV intensity and for the pre-determination of the possible duration of stay in the sun without sunburn.

According to the invention it is intended to use test strips such as those shown for example in FIG. 1a) to determine the current UV intensity in light and to pre-determine the duration of stay in the sun that is possible without sunburn. Such test strips are each essentially composed of a flat, preferably oblong and in particular rectangular foil (2) which carries a matrix (3) containing a photoactive chromogenic substance. With regard to the structure, such test strips have already been known for a long time from analytical chemistry for example as blood or urea test strips. Whereas such test strips can have very different dimensions, test strips used according to the invention have proven to be preferable that are between ca. 2 and 10 cm long and between ca. 3 and 15 mm, preferably between ca. 4 and 8 mm wide. A foil denotes any material which is relatively thin but nevertheless has a rigidity which makes it suitable for the intended handling. Thus such foils can be composed of wood, glass, metal or plastic. Plastic foils are particularly preferred such as for example polystyrene, polyester or polyethylene which are between about 0.2 and 0.5 mm thick.

The foil (2) carries a matrix composed of an absorptive or swellable material. Porous or non-porous films or membranes, fleeces, fabrics or tissues come into consideration. A matrix made of a polyester fleece has proven to be particularly suitable within the scope of the invention. The matrix material as part of the test strip can be between ca. 0.1 and 0.8 mm thick and have a rectangular or quadrangular area between ca. 9 and 250 mm$^2$. Matrix materials are particularly preferred which are between ca. 0.3 and 0.6 mm thick and between ca. 16 and 36 mm$^2$ in size. Whereas it is in principle possible to mount this matrix (3) on any desired site of a foil (2), it has proven to be particularly suitable for the purpose according to the invention to attach the matrix (3) at or near one end of an oblong foil (2). The attachment can be carried out by glueing the matrix to the foil or also by clamping the matrix between the foil and a material stretched thereover. In the latter case it is of course necessary to take care that the material stretched thereover is permeable to UV light. However, it is particularly preferred to glue the matrix (3) to the foil (2). This can be achieved directly, for example by means of a melt adhesive between matrix and foil, for example by thermally melting an adhesive layer of a foil coated for this purpose or also by a double-sided adhesive tape between matrix and foil. The latter is a particularly preferred embodiment.

The matrix (3) of the test strip (1) which can be used according to the invention carries a photoactive substance i.e. a substance which is changed by exposure to sunlight. Those substances are preferably used for the present invention which change their colour on exposure to sunlight. Such substances are denoted chromogenic, whereby a colour change is understood as a change from one colour to another as well as the formation of a colour from a previously colourless substance and also as a previously coloured substance becoming colourless. Within the scope of the invention those substances have proven to be particularly suitable which are stable towards humidity and temperature influences and which yield visually readily-recognizable colour gradations depending on the sunlight intensity within particular time periods. Of course those substances are especially preferred which selectively absorb the so-called UV-B radiation (wavelength between 280 and 320 nm) and UV-A radiation (wavelengths between 320 and 400 nm), in particular short-wave UV-A radiation. In this sense 2,18-phosphoromolybdic acid (18-molybdodiphosphoric acid) is excellently suitable as the photoactive chromogenic substance which changes its colour depending on the sunlight intensity and exposure period from light yellow through light blue to dark blue. Test strips with this substance are known from EP-A 0 431 456 for the colorimetric determination of glucose in body fluids. The substance is denoted there as 18-molybdodiphosphoric acid.

According to the invention the photoactive chromogenic substance can be coated on the matrix (3) However, the matrix (3) is preferably impregnated with a solution or suspension of the substance in a suitable solvent or dipersant.

Figure 1B:
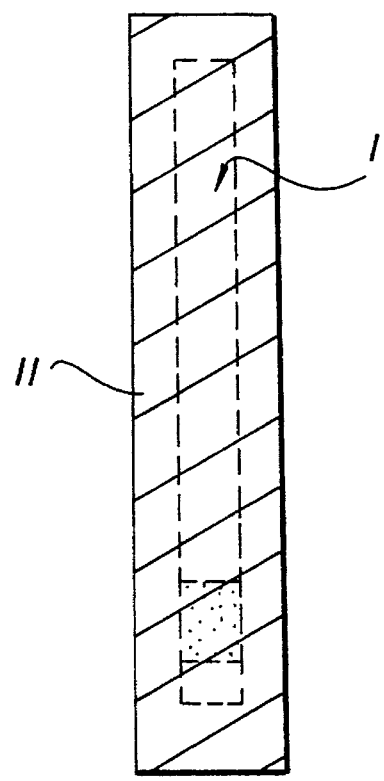
FIG. 1b) shows a test strip individually packaged in packaging material

Since, in order to pre-determine the possible duration of stay in the sun without sunburn, the test strips contain a photoactive substance, it is advisable to store the test strips protected from light. The test strips (1) according to FIG. 1b) are preferably offered for sale packaged in such a way that no light reaches the photoactive substance. In addition the test strips should be protected from humidity during their storage. Therefore each test strip is preferably offered for sale individually packaged in packaging material (11). Aluminium foils which are impermeable to humidity and light have proven to be advantageous as the packaging material (11) with which the test strips (1) can be individually packaged. A packaged test strip (1) is shown in FIG 1b). This is located between two non-transparent foils which are joined together around the test strip and thus enclose the test strip (1) on all sides and isolate it against environmental influences in particular against light and humidity.

Figure 2:
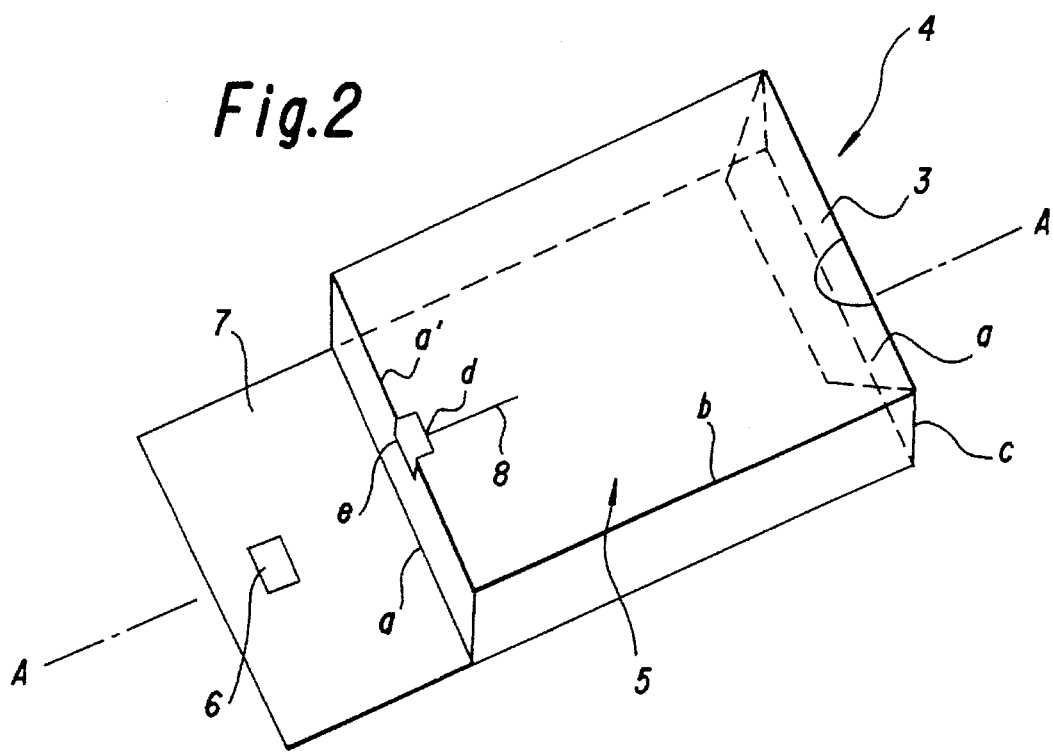
FIG. 2) shows a test strip pack

A test system according to the invention to pre-determine the duration of stay in the sun without sunburn contains the previously described test strips preferably individually packaged in packaging material (11) and a test strip pack which is suitable for holding the test strips wherein the test strip pack comprises a container to hold the test strips and a device which enables the test strip pack to be hung up on a pin. A test strip pack (4) according to the invention is shown in FIG. 2. It comprises a container (5) in the form of a box which is essentially in the form of a cuboid with edges a), b) and c). A cuboid is usually characterized in that it is bounded by six flat surfaces wherein the edges a), b) and c) can all be of the same or of different length or two can also be the same and one can be of different length. If all three edges have the same length, then it is a cube in which all the boundary surfaces are quadrangular. If all three edges have a different length the six boundary surfaces are in each case three pairs of rectangular surfaces, each pair consisting of two equal rectangular surfaces but the three pairs having different rectangular surfaces when compared with one another.

In the test strip pack (4) according to the invention one of the flat surfaces bounding the cuboid extends beyond the cuboid (7). This surface carries a hanging device (6) which enables the test strip pack (4) to be hung up on a pin. A hole has proven to be particularly advantageous as the hanging device (6). A hole which is designed such that a test strip (1) as described above fits into this hole is particularly preferred as the hanging device (6). The dimensions of this hole should be advantageously such that it is possible to pass the strip through the hole and that the test strip is guided to a certain extent in this process. This means that the test strip can be pulled endwise through the hole in such a way that both longitudinal sides of the test strip brush the walls of the hole.

In the container (5) of the test strip pack (4) according to the invention the regular edge of the cuboid (a') which is nearest to the hanging device (6) is replaced completely or partially by two edges (d, e) which are essentially parallel to one another and to the regular edge of the cuboid. One can for example envisage that a partial replacement of the regular edge of the cuboid (a') is achieved by cutting out a piece of this edge. Such a partial replacement of the regular edge (a') is particularly preferred.

Figure 3:
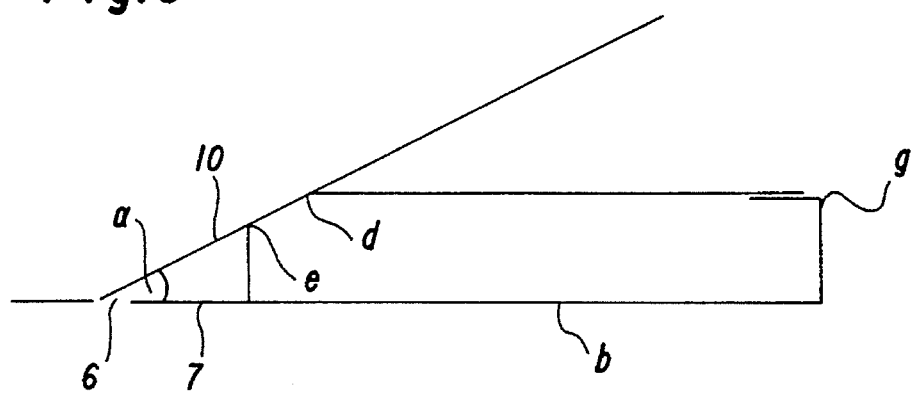
FIG. 3) shows a cross-section through the test strip pack according to FIG. 2) along the line A—A with a straight line through the hanging device over edges a and d, FIG. 4) shows a further embodiment of a test strip pack and FIG. 5) shows a test strip pack with a test strip placed thereon to carry out the determination according to the invention.
Figure 4:
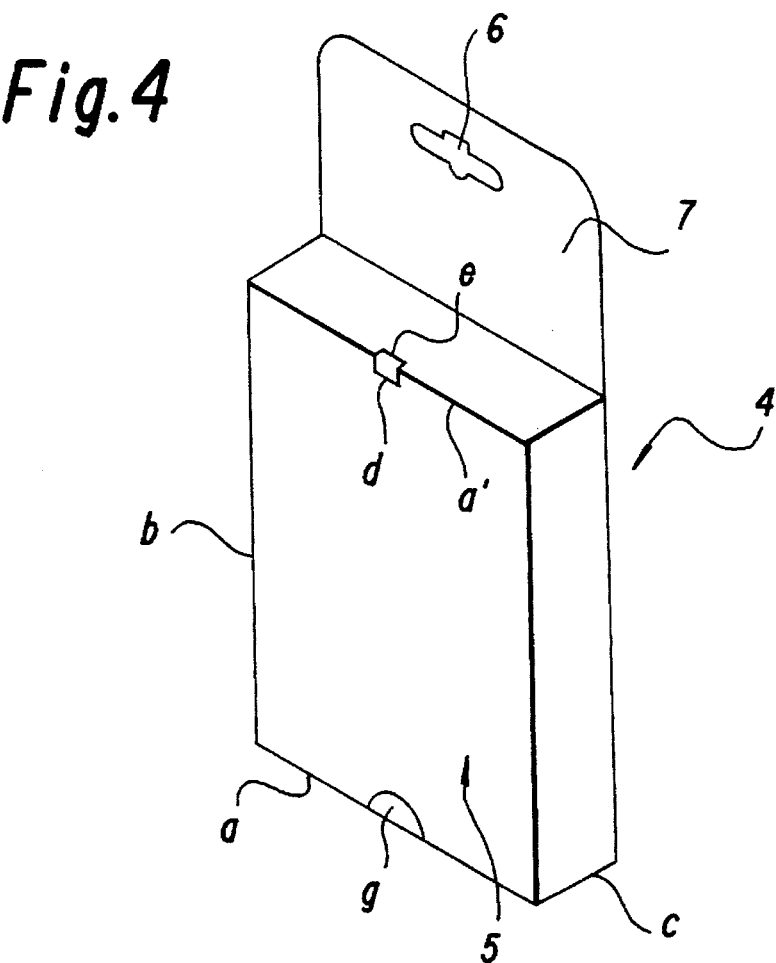

In the test strip pack (4) according to the invention, the hanging device (6) and one or both of the parallel edges (d, e) are in such a geometric relation to one another that a straight line (10) from one or both parallel edges aimed through the hanging device forms a particular angle ($\alpha$) to the flat surface (7) protruding beyond the cuboid borders. This is shown schematically in FIG. 3. The straight line (10) touches in this case both parallel edges (d, e) and the hanging device (6). However, it is also possible according to the invention that the straight line (10) only lies on one of the edges (d, e). This is then conceivable when the edge (d) is not high enough to touch the straight line resting on the edge (e) or when edge (e) is not high enough to touch the straight line resting on the edge (d). In any case the straight line (10) forms a particular angle ($\alpha$) to the flat surface (7) protruding beyond the cuboid border. This angle ($\alpha$) is between ca. 10 and 40 degrees, preferably between ca. 20 and 30 degrees.

A pack (4) according to the invention is particularly preferred in which the container (5) is a cuboid box in which at least one of the boundary, surfaces is in the form of a flap (9). This flap (9) can be in the form of a tongue which can be opened up in order to withdraw test strips from the container (5) and can be closed again by subsequently pushing the tongue back. The boundary surface located furthest away from the hanging device is preferably in the form of such a flap (9).

Basically any material can be used as the material for the test strip pack (4) which has a certain intrinsic rigidity so that the form of the test strip pack is also maintained after its manufacture. Conceivable materials are above all plastic and paper, paper and in particular cardboard having proven to be particularly preferred since this material can easily be brought into the appropriate form after cutting by folding and glueing.

Paper and in particular cardboard have also proven to be preferable because this material can easily be printed on. Thus for example it is easy to print a line (8) on the surface opposite to the surface extending beyond the cuboid that points to the hanging device (6). This line should be preferably arranged so that it corresponds to the projection of the straight line (10) that extends from the hanging device (6) over the edges (d, e) on the surface formed by the edges a and b i.e. it corresponds to the surface opposite to the surface extending beyond the cuboid.

Since it is intended that the test strip pack (4) should be suitable for holding test strips to pre-determine the possible duration of stay in the sun without sunburn it is obvious that the dimensions of the test strip pack (4) have to be correspondingly matched to the dimensions of the test strips. Edge lengths for "a" between ca. 70 and 90 mm for b between ca. 150 and 170 mm and for c between ca. 15 and 25 mm have proven to be advantageous for the container (5). The shortest distance between the hanging device (6) and the next boundary surface of the cuboid container (5) is advantageously about 40 mm. The cardboard which is particularly preferably used for the test strip pack (4) has a thickness of about 0.35 mm. If the regular edge of the cuboid (a') nearest to the hanging device (6) is partially replaced by two edges which are essentially parallel to each other and to the regular edge of the cuboid then the respective length of the two parallel edges (d, e) is between ca. 3 and 15 mm, preferably between ca. 4 and 8 mm. They are matched to the width of the test strips.

The test strips which can be used according to the invention enable the current UV intensity of light to be determined since the colour of the matrix of the test strip changes to a variable extent within a given time period at different UV intensities. Using a colour comparison scale which was set up with known UV intensities, it is possible to also determine unknown UV intensities in this way.

The method according to the invention to pre-determine the maximum possible duration of stay in the sun without sunburn is carried out by exposing a test strip of the previously described type comprising a flat, preferably oblong foil which carries a matrix containing a photoactive chromogenic substance to sunlight for a particular period. This results in a change in the colour of the photoactive chromogenic substance in the matrix. The resulting change in colour is compared with a colour comparison scale. Caucasian, i.e. people of or relating to the white race including persons of European, north African or southwest Asian ancestry can be divided into 4 skin types with regard to their skin tanning behaviour and their sensitivity to sunburn:

| Skin type | Skin reaction and ethnic classification |
| --- | --- |
| I | Always a rapid sunburn, slight or no tanning even after repeated irradiation (Celtic type) |
| II | Almost always sunburn, moderate tanning after repeated irradiation (pale-skinned, European type) |
| III | Sunburn moderately frequently, increasing tanning after repeated irradiation (dark-skinned European type) |
| IV | Seldom sunburn, tanning begins rapidly and is significant (Mediterranean type) |

This classification of types is used worldwide. It is also advantageous to include instructions for the determination of the skin type of a particular person in the test system according to the invention.

Due to the 4 possible different skin types, the test system according to the invention should contain colour comparison scales for the various skin types. These depict various colour gradations for a skin type which represent the possible colours of the matrix containing the photoactive chromogenic substance after a particular period of exposure. Each colour corresponds to a particular UV intensity from which it is possible to deduce how long a person of a particular skin type can spend in the sun without getting sunburnt. In this respect each colour zone of the colour comparison scale is assigned an exact time which gives the possible duration of stay in the sun without sunburn. The practical procedure in the method to pre-determine the maximum possible duration of stay in the sun without sunburn when the skin type of a person is known is thus to compare the corresponding colour comparison scale with the colour of the matrix of the test strip which has been exposed for a certain time to sunlight. The colour of the zone of the colour comparison scale which is closest to the colour of the matrix containing the photo-active chromogenic substance then gives the period during which it is possible to stay in the sun without sunburn. Especially test strips containing 2, 18-phosphoromolybdic acid (18-molybdodiphosphoric acid) take into account the UV-A-radiation responsible for skin ageing. Allowance is made for this radiation on the colour comparison scale in relation to the declared time. If this allowance is not made the recommended times can be about 40 to 60% higher.

Figure 5:
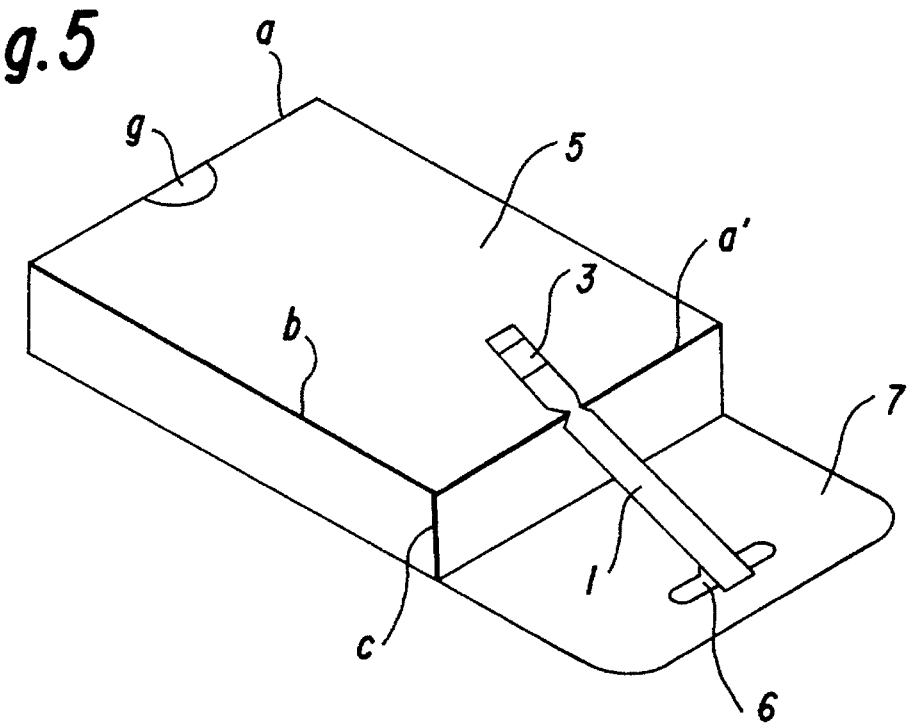

The method according to the invention is particularly preferably carried out in such a way that the test strip is aligned with the sun in such a way that the incident light is as perpendicular as possible to the matrix containing the photoactive chromogenic substance. Such an alignment can be achieved particularly simply with the aid of the test strip pack according to the invention which is placed on a foundation which is as horizontal as possible such as for example the ground or the surface or a table. The test strip is placed on one or both parallel edges which replace the regular cuboid edge (a') of the container or the test strip pack in such a way that it extends into the hanging device of the test strip pack. The test strip is held at an inclination in such a way that as much light as possible falls on the matrix containing the photoactive chromogenic substance. A corresponding embodiment is shown in FIG. 5. In order to align the test strip pack with the inserted test strip with the sun it is especially advantageous to utilize the line located on the surface opposite to the surface extending beyond the cuboid. The inserted test strip can namely act like the pointer of a sundial. The pack is turned in such a way that the shadow of the test strip is brought into coincidence with the line on the surface of the box, then the strip is optimally aligned.

Figure 6:
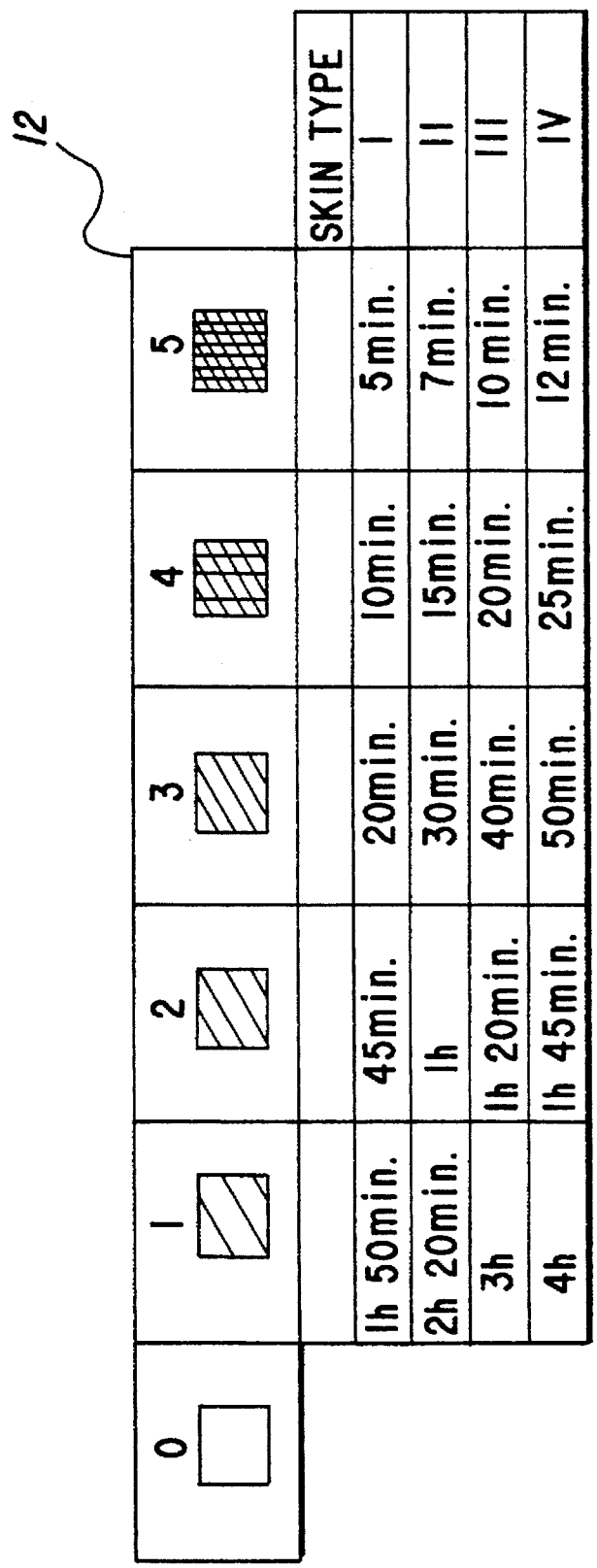
FIG. 6) shows a colour comparison scale combined with a table correlating skin type, colour intensity and maximum possible duration of stay in the sun without sunburn.

After 5 minutes the colour on the strip is compared with the colours of the colour comparison scale (12) as it is depicted in FIG. 6. The strip should be removed from direct sunlight as otherwise the colour will become darker.

Once the colour of the exposed strip has been correlated with one of the colourfields 1 to 5 of the colour comparison scale (12) and once the skin type of the person in question has been identified as being I, II, III or IV then the length of time the corresponding person may spend in the sun without getting sunburned may be identified in the table as shown in FIG. 6. For example when the test strip shows a colour intensity comparable to field 3 a person with skin type I may spend only 20 minutes in the sun whereas a person with skin type III may spend 40 minutes in the sun without getting sunburned. If a sun protecting agent is used the possible stay in the sun results when the time value according to the table of FIG. 6 is multiplied by the sun protection factor of the agent.

Field 0 of the colour comparison scale (12) represents the colour of the original, unused test strip.

The advantage of the test system according to the invention is that under many typical holiday conditions an individual prognosis of the harmless period of stay in the sun can be made cheaply. The test system is small and convenient so that it can always be carried with one. Since, it is possible to align the test strip with the, sun with the aid of the test strip pack it is possible to easily and reproducibly pre-determined time period which one can ray in the sun without having apprehensions about sunburn in regions boy, vein ca. 60° northern and 60° southern latitude. Independent of the geographical latitude, the short-wave UV radiation also increases very greatly with the height above sea level. This increase can be up to 20% per 1000 m. In addition what is important for UV radiation and its effect on humans is the topography and the nature of the ground at the site of measurement. Hence the test system according to the invention can also be used advantageously in mountaineering, and winter sports.

It is intended to dispense with the advantages of the test strip pack, a test system is of course also possible according to the invention which contains test strips for the determination of the UV intensity and for the pre-determination of the possible duration of stay in the sun without sunburn that are essentially composed of a flat, preferably oblong foil (2) carrying a matrix (3) containing a photoactive chromogenic substance, if desired, individually packaged in packaging material (11) and a colour comparison scale with several colour zones, the individual colour zones being assigned numerical values which give the possible period which a person can remain in the sun without sunburn. The test strips, their optional individual packaging and the colour comparison scale and the use thereof correspond completely with the, aforementioned. In this respect such a simplified test system can also contain several colour comparison scales which are aimed at individual skin types.

As used in the present application, the term "sunburn" is intended to mean an injury to the skin produced by ultra-violet rays following excessive exposure to sunlight, with erythema, tenderness and sometimes blistering.

The test system according to the present invention is intended to be marketed with instructions for use. An example of instructions, which would be included in a test kit, for the determination of an individual's skin type and for use of the test system of the present invention are as follows:

Instructions for use of the Test Strips

In recent years, the public's attention has been increasingly drawn to the effect of UV rays on the skin. Increasingly more reports on the higher frequency of skin cancer are being published. Scientists believe the reason for this phenomenon lies in the reduction of the ozone layer in higher regions of the atmosphere.

Sunlight has a positive influence on our physical and psychological characteristics. Nowadays, a suntan is important to many of us. Holidays, in particular, are used to become brown as quickly and intensively as possible. In such situations, the sensible application of sun protecting preparations such as creams, lotions and oils etc. is indispensable.

Depending on your skin type, the sun protection factor in creams, lotions etc. and the UV intensity, you can only stay in the sun for a certain period of time without getting sunburned. The sun protection factor is known and the skin type can be seen from the appended table. The UV intensity is the only factor about which the sunbather is unsure.

The present test strips are a great help as they change color when subjected to UV light. The color on the strip becomes deeper depending on the intensity of UV rays and the period during which you may stay in such conditions is thus shortened accordingly.

The test strips register the UVB rays, which cause sunburn, as well as UVA rays. Long periods of exposure to UVA can cause damage at a later stage (ageing of the skin).

How to use the test strips:

Find your skin type first by using the table below. Expose the testpad on the test strip to direct sunlight. You can use the slit on the box to fix the strip. Make sure that the sun shines from a vertical angle (straight down). After 5 minutes, the color on the strip is compared with the colors on the reverse side of the pack. The strip should be removed from direct sunlight as otherwise the color will become darker.

Once you have found the column, move up to your skin type where the length of time you may spend in this sun intensity without getting sunburned is stated in minutes.

If you use a sun protecting agent, you may stay in the sun under these conditions for the amount of time longer stated by the sun protection factor of the sun protecting agent.

Important:

The test strips warn you about UV rays but do not provide protection against them.

The risk of getting sunburned is particularly high during the first few days of your holiday. If in doubt, always stay in the sun for a shorter period.

The test strips are not suitable for use with tanning devices of any nature (e.g., sunbeds).

The stated times do not apply to those who suffer from sun allergies. Please consult your doctor in this respect.

If the skin is already slightly tanned, the next higher skin type on the enclosed table can be selected.

Further Information:

If you use a sun protecting agent, it should be applied at least 30 minutes before you sunbathe. It should then be re-applied regularly, and particularly after swimming. The skin's sensitivity to the sun is greater after swimming.

Refrain from wearing perfumes when sun bathing as this could cause marks to appear on the skin.

Some medicines, particularly antibiotics, rheumatism medication and psychopharmaceuticals, increase the skin's sensitivity to sunlight. Consult your physician if in doubt. The risk of cancer is particularly increased among children under the age of 10 who get sunburned.

| Skin type | | | |
|---|---|---|---|
| Skin type | Description | Sunburn | Suntan |
| I | Very fair and pale skin lots of freckles red hair green/blue eyes | Always badly | None |
| II | Fair skin freckles rare blond/brown hair blue/green/grey eyes | Usually badly | Hardly |
| III | Fair/light brown skin no freckles dark blond/brown hair grey/brown eyes | Seldom | Good |
| IV | Brown/olive skin no freckles dark brown/black hair dark eyes | Hardly | Quick and deep |

According to Kindl/Raab, Light and Skin

We claim:

1. A method for predetermining the length of exposure to sunlight without sunburn for a person, comprising the following steps:

exposing to sunlight, a test strip comprising a matrix attached to a flat foil strip, wherein said matrix contains 18-molybdodiphosphoric acid, and comparing any color changes in said photoactive chromogenic substance with a chart which correlates color changes in said photoactive chromogenic substance with the maximum duration of exposure to ultraviolet radiation possible without sunburn to the person.

2. The method according to claim 1 wherein said photoactive chromogenic substance is 18-molybdodiphosphoric acid and wherein said flat foil strip is composed of a substance selected from the group consisting of wood, glass, metal and plastic.

3. The method according to claim 1, wherein said test strip is exposed to sunlight with the aid of a test strip pack comprising a container in the form of a cuboid, wherein a planar surface extends beyond the cuboid and contains a structure for hanging said container and wherein the edge of the cuboid parallel to said planar surface which extends beyond the cuboid and nearest to said structure for hanging said container contains a notch which is positioned such that a straight line from said notch, passing through the structure for hanging the container, forms an angle of between 10–40 degrees to the flat surface which extends beyond the cuboid, and wherein said flat foil strip is aligned such that sunlight falls as perpendicularly as possible on said matrix containing said photoactive chromogenic substance.

4. The method according to claim 3, wherein said test strip is placed in said notch in such a way that it extends into the structure for hanging the container.

5. The method according to claim 3, wherein said angle is between 20–30 degrees.

6. A method for determining the intensity of ultraviolet radiation, comprising the following steps:

exposing to ultraviolet radiation, a test strip comprising a matrix attached to a flat foil strip, wherein said matrix contains 18-molybdodiphosphoric acid, and comparing any color changes in said photoactive chromogenic substance with a chart which correlates color changes in said photoactive chromogenic substance with the intensity of ultraviolet radiation.

7. A method for predetermining the length of exposure to sunlight without sunburn for a person, in the presence of a substance which blocks ultraviolet radiation on the person's exposed skin, comprising the following steps:

coating a test strip comprising a matrix sandwiched between a flat foil strip and a UV permeable, moisture impermeable material, with a substance which blocks ultraviolet radiation, wherein said matrix contains 18-molybdodiphosphoric acid, exposing said test strip to sunlight, and comparing any color changes in said photoactive chromogenic substance with a chart which correlates color changes in said photoactive chromogenic substance with the maximum duration of exposure to ultraviolet radiation possible without sunburn.

* * * * *